US00PP11750P2

(12) United States Plant Patent

Sorensen

(10) Patent No.: US PP11,750 P2
(45) Date of Patent: Jan. 23, 2001

(54) OSTEOSPERMUM PLANT NAMED 'NINDA'

(75) Inventor: Carl Aksel Kragh Sorensen, Aabyhoj (DK)

(73) Assignee: Paul Ecke Ranch, Inc., Encinitas, CA (US)

( * ) Notice: Under 35 U.S.C. 154(b), the term of this patent shall be extended for 0 days.

(21) Appl. No.: 09/291,103

(22) Filed: Apr. 14, 1999

(51) Int. Cl.[7] ..... A01H 5/00

(52) U.S. Cl. ..... Plt./360

(58) Field of Search ..... Plt./360

(56) References Cited

PUBLICATIONS

UPOV CD–ROM, PBR 970883, Osteospermum designated Ninda, 1997.*

* cited by examiner

*Primary Examiner*—Bruce R. Campell
*Assistant Examiner*—Melissa L. Kimball
(74) *Attorney, Agent, or Firm*—C. A. Whealy

(57) ABSTRACT

A distinct cultivar of *Osteospermum* plant named 'Ninda', characterized by its compact and upright plant habit; numerous inflorescences per plant; white ray florets with pink lavender apices and a pink lavender base giving the appearance of a small ring around the blue disc; and inflorescences that do not close at night.

1 Drawing Sheet

BACKGROUND OF THE INVENTION

The present invention relates to a new and distinct cultivar of Osteospermum plant, botanically known as *Osteospermum ecklonis* and referred to by the cultivar name Ninda.

The new cultivar is a product of a planned breeding program conducted by the Inventor in Aabyhoj, Denmark. The objective of the breeding program was to create new compact Osteospermum cultivars with interesting ray floret colors.

The new cultivar originated from a cross made by the Inventor in 1995 of a proprietary selection of *Osteospermum ecklonis* identified as 9302A as the female, or seed, parent and a proprietary selection of *Osteospermum ecklonis* identified as 949314 as the male, or pollen, parent. The new Osteospermum was selected by the Inventor as a flowering plant within the progeny of this cross in a controlled environment in Aabyhoj, Denmark, in 1996.

Plants of the new cultivar are different from plants of the female parent, the selection 9302A, in growth habit, inflorescence size and ray floret color.

Plants of the new Osteospermum are different from plants of the male parent, the selection 949314, in plant height, ray floret color and quantity of ray florets.

Asexual propagation of the new cultivar by terminal cuttings at Aabyhoj, has shown that the unique features of this new Osteospermum are stable and reproduced true to type in successive generations.

SUMMARY OF THE INVENTION

The following traits have been repeatedly observed and are determined to be the unique characteristics of 'Ninda'. These characteristics in combination distinguish 'Ninda' as a new and distinct cultivar:

1. Compact and upright plant habit.
2. Numerous inflorescences per plant.
3. White ray florets with pink lavender apices and a pink lavender base giving the appearance of a small ring around the blue disc.
4. Inflorescences that do not close at night.

The new cultivar can be compared to the Osteospermum cultivar Cape Daisy Nairobi, disclosed in U.S. Plant Pat. No. 10,340. In side-by-side comparisons conducted in Encinitas, Calif., plants of the new cultivar are more upright, slightly taller and more uniform; shorter and wider leaves; and larger inflorescences than plants of the cultivar Cape Daisy Nairobi. In addition, ray florets of the new Osteospermum are ligulate, entire and not spoon-shaped like ray florets of the cultivar Cape Daisy Nairobi.

The cultivar Ninda has not been observed under all possible environmental conditions. The phenotype may vary somewhat with variations in environment such as temperature, daylength and light intensity, without, however, any variance in genotype.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph at the top of the sheet comprises a side perspective view of a typical flowering plant of 'Ninda'.

The photograph at the bottom of the sheet is a close-up view of typical inflorescences and young and mature leaves of 'Ninda' (code number 9601 in the photograph) and 'Cape Daisy Nairobi' (Nairobi in the photograph). Foliage and floret colors in the photographs may appear different from the actual colors due to light reflectance.

DETAILED BOTANICAL DESCRIPTION

The following observations, measurements and values describe one-gallon containers of the new cultivar grown in Encinitas, Calif., under outdoor, full-sun conditions with day temperatures ranging from 20 to 27° C. and night temperatures ranging from 6 to 14° C. Plants were pinched (terminal apex removed) one time about two weeks after planting rooted cuttings. Plants used for this description were grown for about 12 to 14 weeks after planting rooted cuttings.

Color references are made to The Royal Horticultural Society Colour Chart except where general terms of ordinary dictionary significance are used.

Botanical classification: *Osteospermum ecklonis* cultivar Ninda.

Parentage:

*Female, or seed, parent.*—Proprietary selection of *Osteospermum ecklonis* identified as 9302A.

*Male, or pollen, parent.*—Proprietary selection of *Osteospermum ecklonis* identified as 949314.

Propagation:

*Type.*—By terminal cuttings.

*Time to initiate roots.*—About 10 days at 18° C.

*Time to develop roots.*—About 21 days at 18° C.

*Rooting habit.*—Fibrous.

Plant description:

*Appearance.*—Perennial herbaceous container and garden plant. Broad inverted triangle. Upright with rounded canopy; uniform. Freely branching with about nine primary and about 12 secondary branches. Full plants with dense foliage and erect flower stems.

*Vigor.*—Moderately vigorous.

*Plant height.*—About 34 cm.

*Plant spread.*—About 46 cm.

*Lateral branch description.*—Length: About 14 to 17 cm. Diameter: Primary, about 8 mm; secondary, about 3 mm. Internode length: About 1 to 2 cm. Texture: Short coarse hairs; woody at base. Color: 144A.

*Foliage description.*—Leaves alternate, single. Quantity of leaves per secondary branch: Numerous, about 34. Length, fully expanded leaves, basal: About 5.5 to 6.5 cm. Width, fully expanded leaves, basal: About 2.5 to 3 cm. Shape: Elliptic to lanceolate. Apex: Broadly acute. Base: Attenuate. Margin: Nearly entire with five to seven widely-spaced irregular teeth. Teeth typically present on older leaves. Aspect: Mostly flat. Texture: Smooth; thick and leathery; slightly pubescent on lower surface. Fragrance: Sweet spicy smell. Color: Young foliage, upper surface: 137A. Young foliage, lower surface: 137B. Fully expanded foliage, upper surface: 137A. Fully expanded foliage, lower surface: 137B. Attenuated leaf base: 143C. Venation, upper and lower surfaces: 143B.

Inflorescence description:

*Appearance.*—Daisy-type composite inflorescence form; actinomorphic. Single inflorescences displayed above foliage, upright on long peduncles arising from leaf axils. Disc and ray florets arranged acropetally on a capitulum. Typically about 77 opened and unopened inflorescences per plant. Inflorescences last about one week. Inflorescences persistent. Inflorescences not night-closing.

*Flowering response.*—Plants flower continuously from April to October in the Northern Hemisphere.

*Fragrance.*—Very faint.

*Inflorescence size.*—Diameter: About 6.5 cm. Depth (height): About 1.5 cm. Diameter of disc: About 1.2 to 1.4 cm.

*Inflorescence buds.*—Length: About 1.8 cm. Width: About 1 cm. Shape: Ovoid. Color: 90A.

*Ray florets.*—Length: About 2.8 to 3 cm. Width: About 9 mm. Shape: Ligulate. Apex: Tri-dentate, minute. Base: Acute. Margin: Entire. Aspect: Flat to upright. Texture: Smooth, satiny. Number of ray florets per inflorescence: About 21 in two whorls. Color: When opening, upper surface: 155C. When opening, lower surface: 86A. Fully opened, upper surface: White, 155C to 155D, with pink lavender, 84B, at apex and base. Colored base gives the appearance of a small pink lavender ring around the bluish disc. Fully opened, lower surface: Central longitudinal stripe, 81C, surrounded by 83A on either side.

*Disc florets.*—Shape: Tubular; slightly salverform; five-lobed, fluted at apex. Number of disc florets per inflorescence: Numerous, about 88. Length: About 5 mm. Width: About 1.5 to 2 mm. Color: Immature: Apex, 86A; midsection, 84D. Mature: Apex, 86B; midsection, 84B.

*Phyllaries.—Shape: Linear. Apex: Narrowly acute. Margin: Entire. Quantity and arrangement: About* 21 per inflorescence; whorled. Texture: Hirsute. Color: Upper surface: 138C. Lower surface: 138A.

*Peduncle.*—Length: About 8.5 to 9 cm. Aspect: Moderately strong; inflorescences held above foliage. Texture: Hispid; coarse. Color: 144A.

*Reproductive organs.*—Androecium: Present on disc florets only. Stamens: Five; fused. Anther shape: Oblong. Anther size: About 1.5 mm. Anther color: 86A. Pollen amount: Abundant. Pollen color: 14A. Gynoecium: Present on ray and disc florets. Pistils: One. Pistil length: About 4 mm. Stigma shape: Bipartate. Stigma color: 86A. Style length: About 3 mm. Style color: 86A. Ovary color: 1D. Seed, immature: Length: About 6 mm. Diameter: About 3 mm. Color: Green.

Disease resistance: Resistance to pathogens common to Osteospermum has not been observed on plants of the new Osteospermum.

It is claimed:

1. A new and distinct cultivar of Osteospermum plant named 'Ninda', as illustrated and described.

* * * * *

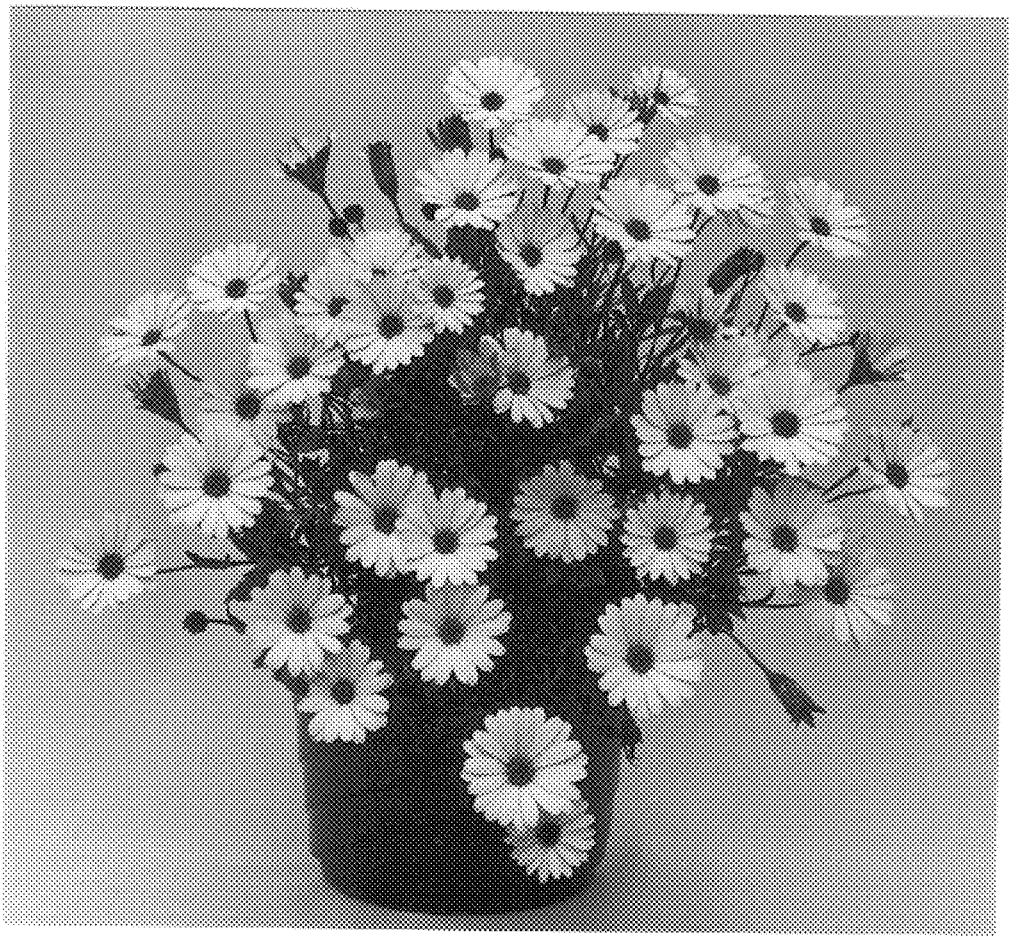
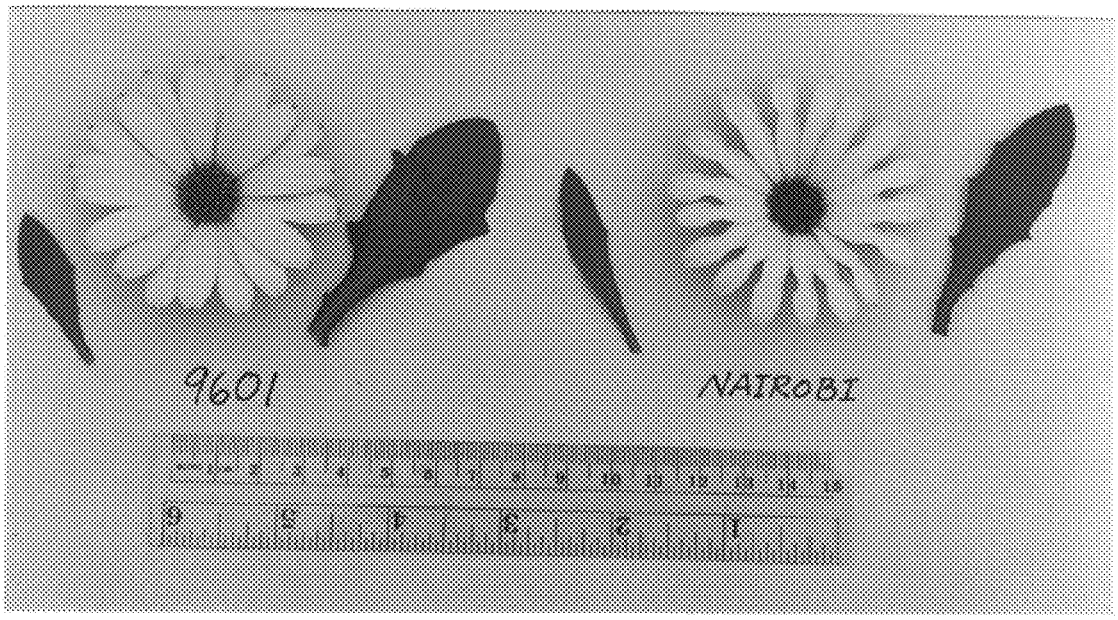
9601
NAIROBI